United States Patent
Suzuki (10) Patent No.: US 7,427,607 B2
(45) Date of Patent: Sep. 23, 2008

(54) DRUG ADMINISTRATION METHOD

(75) Inventor: Shigeki Suzuki, Tokyo (JP)

(73) Assignee: Next21 K.K., Tokyo (JP)

( * ) Notice: Subject to any disclaimer, the term of this patent is extended or adjusted under 35 U.S.C. 154(b) by 260 days.

(21) Appl. No.: 10/505,205

(22) PCT Filed: Feb. 18, 2003

(86) PCT No.: PCT/JP03/01693

§ 371 (c)(1),
(2), (4) Date: Feb. 1, 2005

(87) PCT Pub. No.: WO03/070110

PCT Pub. Date: Aug. 28, 2003

(65) Prior Publication Data

US 2005/0123485 A1    Jun. 9, 2005

(30) Foreign Application Priority Data

Feb. 20, 2002  (JP)  ............................. 2002-042480

(51) Int. Cl.
| | |
|---|---|
| *A61K 47/38* | (2006.01) |
| *A61K 47/36* | (2006.01) |
| *A61K 47/26* | (2006.01) |
| *A61K 47/42* | (2006.01) |
| *A61K 51/08* | (2006.01) |
| *A61K 9/00* | (2006.01) |
| *A61K 9/10* | (2006.01) |
| *A61K 9/12* | (2006.01) |
| *A61K 9/14* | (2006.01) |

(52) U.S. Cl. .............................. 514/57; 514/2; 514/23; 514/44; 514/54; 514/55; 514/59; 424/43; 424/46; 424/400; 424/489

(58) Field of Classification Search ................... 424/43, 424/46, 401, 489; 514/2, 23, 44, 54, 55, 514/57, 59

See application file for complete search history.

(56) References Cited

U.S. PATENT DOCUMENTS

| | | | | | |
|---|---|---|---|---|---|
| 4,427,651 | A | * | 1/1984 | Stroetmann | .................. 424/46 |
| 5,484,913 | A | * | 1/1996 | Stilwell et al. | ................. 536/57 |
| 5,645,051 | A | | 7/1997 | Schultz et al. | |
| 5,652,274 | A | * | 7/1997 | Martin | ....................... 514/724 |
| 5,891,460 | A | * | 4/1999 | Rodgers et al. | ............. 424/445 |
| 5,951,531 | A | * | 9/1999 | Ferdman et al. | ............. 604/290 |
| 5,980,625 | A | * | 11/1999 | Sawamura et al. | ............ 106/35 |
| 6,403,570 | B1 | * | 6/2002 | Soe et al. | ....................... 514/57 |
| 6,566,652 | B1 | * | 5/2003 | Kato | ........................... 250/288 |
| 6,797,258 | B2 | * | 9/2004 | Platz et al. | ..................... 424/45 |
| 7,195,912 | B2 | * | 3/2007 | Takezawa et al. | ........... 435/397 |

FOREIGN PATENT DOCUMENTS

| | | | |
|---|---|---|---|
| JP | 2003062057 | * | 3/2003 |
| WO | WO 94/22427 A1 | | 10/1994 |
| WO | WO 98/31414 A1 | | 7/1998 |

* cited by examiner

*Primary Examiner*—Johann Richter
*Assistant Examiner*—James H Alstrum
(74) *Attorney, Agent, or Firm*—Ostrager Chong Flaherty & Broitman P.C.

(57) ABSTRACT

A method of administering a drug whereby a fine drug powder can be accurately administered to a target site (in particular, a target site in the body cavity) via fluidization and spraying with a gas by using a micro tube. Concerning the administration mode, in particular, the drug alone or a biopolymer is administered or the biopolymer is employed as a carrier in the above method. More specifically speaking, a method of administering a fine drug powder which comprises finely milling one or more types fine particles of the drug and/or the biopolymer, blending them each other, fluidizing the blend with a gas, then transporting the fluidized matter in a micro tube by the gas stream and spraying the fine drug powder from the tip of the micro tube toward the target site. Further, an administration method which comprises concentrically providing a capillary tube in the micro tube, supplying an aqueous solution of the drug and/or the biopolymer from the capillary tube into the gas stream and then mixing it with other fine particles of the drug and/or the biopolymer under transportation by the gas.

10 Claims, 3 Drawing Sheets

DRUG ADMINISTRATION METHOD

DESCRIPTION OF THE PRIOR ART

1. Field of the Invention

The present invention relates to a drug administration method, in which a finely powdered drug can be precisely administered to a target site, particularly a target site located within a body cavity, via the utilization of a fluidization process and/or a spraying process that uses a gas within a micro tube. Specifically, the present invention relates to a drug and a method for administering a biopolymer, whereby a single drug or a biopolymer, or a drug with a biopolymer as its carrier, can be sprayed, or whereby fine particles, solutions of a plurality of drugs or mixtures thereof can be sprayed.

2. Background of the Invention

Biopolymers that typically include polysaccharides or proteins with biocompatibilities such as oxycellulose, carboxymetylcellulose, hyaluronic acid, collagens and the like have traditionally been used for various types of applications. For example, JP-A-H09-328,432 (1997) discloses a sprayed drug containing chitin as a hemostat that has a spraying agent filled therein; JP-A-2000-186,048 discloses a hemostat comprising of a poly cationic compound powder and a poly anionic compound powder; and JP-A-H07-155,377 (1995) discloses a powder sprayer for spraying finely powdered particles such as a hemostat or the like into the interior of a body cavity and the nozzle for spraying the powder. Further, for example, U.S. Pat. Nos. 4,657,548, 5,582,591, 6,365,187, 6,372,718, 6,403,570, U.S. Patent Pre-Grant Publication No. 20010000142A1 and U.S. Patent Pre-Grant Publication No. 20010006957A1 disclose various types of biopolymers that possess bioadhesiveness or those employed as hemostats. Because these biopolymers have hemostatic functions or functions for adhesion prevention, they have been applied to surgical operation sites or wound sites as applications for providing hemostasis, preventing adhesion, preventing keloid, wound healing, wound closing, and providing seals and the like.

On the other hand, different types of application format for these biopolymers were required depending upon their respective purpose of use, thus, the various application formats such as non woven sheet-type, film-type, granule-type or gel-type have been developed. Thus, applications thereof were limited by their respective purpose of use, and therefore biopolymers were not able to be generally and widely applied when conducting hemostasis and/or preventing adhesions.

Particularly, the target sites for applying these biopolymers are diversified by size, shape, position of application and the like, thus, there is a wide range of changes. Therefore, it is difficult to precisely attach and/or retain the biopolymer to the target position. Specifically, it should be emphasized that it is almost impossible to apply biopolymers to applications for conducting hemostasis or preventing adhesions within body cavities or at endoscopic post-operation sites.

The present inventor actively conducted development for the provision of a technology, whereby biopolymers could precisely be attached or retained regardless of the size, shape or position of the application site and the inventor eventually found that the biopolymer can be applied to the target site in an extremely easy way by designing the biopolymer with ultra fine particles capable of being fluidized by the jet force of a gas, and spraying the fine particles to the interior of the body cavity or to the surgical site after an operation via endoscope by utilizing gas injection. Based on these developments, the inventor has proposed a type of biopolymer with fine particles, which is capable of providing hemostasis, preventing adhesion, preventing keloid, wound healing, wound closing, and providing seals or the like in an easier way (JP-A-2001-259212).

Meanwhile, there has been no effective method for administering a drug useful in conducting healing for ablated surfaces or a surface of mucosa after ablation by surgical operation. In particular, since systemic administrations such as oral administrations and injection administrations provide lower drug concentrations of administered drugs to the target disease site, a larger dosage is required to obtain higher drug efficacy, resulting in a problem by increasing the opportunity for the manifestation of side effects.

Therefore, in recent years attention has been drawn to technologies for effectively delivering the drug only to the targeted disease site as a means to improve drug efficacy. However, the current situation is that a means for precisely and directly administering the drug to an ablated surface or a surface of mucosa after ablation by a surgical operation has not been developed.

Thus, the present inventor has further developed the former-proposed technologies of fluidization and spraying of fine particles of a biopolymer by a gas, and has found that, in addition to the biopolymer, a drug can also be precisely bound and fixed onto a drug administration site such as a wound face or the like even in the body cavity, and, accordingly, the present invention has been made.

Therefore, in view of the above described situations, it is an object of the present invention to provide a method for precisely administering a finely powdered drug to a target site, in particular to a target site in a body cavity, by utilizing fluidization and injection with a gas and injection with a fine tube (a micro tube) and also to provide a method for administering a biopolymer itself as the drug or administering a drug with a biopolymer as a carrier. More specifically, it is another object of the present invention to provide a method for administering a drug or a biopolymer that is capable of applying a drug or a biopolymer regardless of the size, the shape and the position of the application site and that is capable of providing the target results thereof such as providing a hemostasis, preventing adhesion, preventing a keloid, healing a wound, closing a wound, providing a seal or the like in a easier way.

SUMMARY OF THE INVENTION

In order to solve the problems disclosed in the present application, an aspect of the present invention according to claim 1 is a method for administering a finely powdered drug, characterized in that the drug is pulverized to have a mean particle diameter of equal to or less than 100 µm to provide flowability with a gas, a homogeneous fluid of the fine powder and the gas is prepared and transferred through a micro tube by a flow of the gas, and the finely powdered drug is sprayed on a target site from a tip of the micro tube, the quantity sprayed thereof being adjustable.

Another aspect of the present invention according to claim 2 is a method for administering a biopolymer comprising fluidizing one or more types of fine particles of a biopolymer with a gas to prepare a homogeneous mixed-phase fluid of the biopolymer and the gas; transferring the mixed-phase fluid through a micro tube by flowing the gas; and spraying the fine particles of the biopolymer toward a target site from a tip of the micro tube, thereby providing hemostasis at a wound site, providing a seal thereto, preventing adhesion of an organ and healing a wound.

Specifically, the administration method according to the present invention has a configuration that includes pulverizing the drug and the biopolymer to reduce the unit weight of the pulverized powder, fluidizing thereof with the carrier gas, transferring thereof through the micro tube, and injecting the finely powdered drug and the biopolymer from the tip of the micro tube, and, being so configured, the drug and the biopolymer can be precisely administered through a narrow space from the surface of the body to the target site positioned in a deeper part of the body to which the administration thereof has been conventionally impossible. Various types of biopolymers have been employed for hemostasis, sealing, prevention of the adhesion of an organ, wound healing or the like. The type and the formulation of a plurality of biopolymers for use is different depending on objectives of the medical treatment, and the dosage thereof is also different. However, the method of the present invention, can provide the advantageous effect of precise administration of these biopolymers.

In the administration method according to the present invention, the finely powdered drug can be mixed with the fine particle of the biopolymer as a drug carrier, and administered to the target site by utilizing fluid dynamics of the gas. Therefore, in order to improve an adhesiveness of a drug to a target site, yet other aspect of the present invention according to claim 3 is a method for administering a biopolymer, comprising mixing fine particles of a carrier of a bioabsorbable biopolymer with a finely powdered drug; transferring the powder fluidized with a gas through a micro tube by flowing the gas; and spraying a mixed powder of the biopolymer and the finely powdered drug toward a target site from the tip of the micro tube, thereby providing hemostasis at a wound site, providing a seal thereto, preventing adhesion of an organ and healing a wound.

In the administration method according to the present invention, it was found that vibrating the vessel for mixing the fine particle powder and the gas achieves greater efficiency in the fluidization of the fine particle powder to be administered at a highly reproducible concentration and improves the fluidity thereof with the gas. Therefore, yet other aspect of the present invention according to claim 4 is the method according to any one of claims 1 to 3, wherein a homogeneous fluid of a finely powdered drug and a gas or a homogeneous fluid of a biopolymer and a gas, or a homogeneous fluid of a finely powdered drug and a gas with a biopolymer carrier are prepared by vibrating a mixing vessel for mixing the fine drug powder or the biopolymer and the gas. Vibration can be carried out by, for example, rocking vibration, rotational vibration, ultrasonic vibration or the like.

Further, in the administration method according to the present invention, the spraying of a certain quantity to a target site can be achieved by controlling the concentration of the fluidized powder and the flow rate of the gas for the fine particle powder that is sprayed from the tip of the micro tube. Therefore, yet other aspect of the present invention according to claim 5 is the method according to any one of claims 1 to 3, wherein a quantity of the finely powdered drug or the biopolymer sprayed from the tip of the micro tube is adjusted by adjusting the powder concentration of the fluidized powder and the gas flow.

In the administration method according to the present invention, when the drug or the biopolymer for administration is in a solution form, the solution can be injected into the micro tube through a capillary tube having smaller diameter and disposed within the micro tube, so that the size of the liquid droplets of the solution is reduced by being repeatedly adhered onto and separated from the inner wall of the micro tube by the gas flow, and the droplet is sprayed from the tip of the micro tube, thereby enabling the precise administration to the target site. Therefore, yet other aspect of the present invention according to claim 6 is a method according to any one of claims 1 to 5, wherein a small diameter-tube having a smaller diameter than the micro tube is further provided coaxially in the micro tube, and wherein an aqueous solution of physiological saline, an infusion solution or a drug and/or a biopolymer is injected from the smaller diameter-tube into a gas flow in the smaller diameter-tube, thereby spraying a mixture thereof with the drug in the fluidizing gas and/or the biopolymer fine particles in the micro tube.

On the other hand, in contrast to the above-described approach, a tube having a smaller diameter is coaxially provided in the micro tube, and the fine powder fluidized with the gas is transferred through the smaller diameter tube, and an aqueous solution of the drug, biopolymer or the like is transferred through the clearance between the outer tube (the micro tube) and the inner tube (the smaller diameter tube), and the respective aqueous solutions are mixed at a position in the vicinity of the outlet of the micro tube and sprayed, thereby enabling precise administration to the target site. Therefore, yet other aspect of the present invention according to claim 7 is a method according to any one of claims 1 to 5, wherein a smaller diameter-tube having a smaller diameter than the micro tube is further provided coaxially in the micro tube, wherein the finely powdered drug is transferred by the gas flow through the smaller diameter-tube and an aqueous solution of a physiological saline, an infusion solution or a drug and/or a biopolymer is transferred through the clearance between the inner and the outer tubes, and wherein both of the finely powdered drug and the aqueous solution to be sprayed is mixed at the tip of the micro tube.

Further, yet other aspect of the present invention according to claim 8 is a method according to any one of claims 1 to 7, wherein the drug fluidized with the gas is provided with sustained release, thereby delaying the release of the medicinal properties, and another aspect of the present invention according to claim 9 is a method according to claim 8, wherein the release of the medicinal properties is delayed by microencapsulating, spray drying or freeze drying of the drug.

In addition, a further aspect of the present invention according to claim 10 is a method for administering a drug comprising fluidizing a biopolymer fine powder and fluidizing of a finely powdered drug in different vessels, transferring the respective fine powders by gas flow through a micro tube, spraying the fine powders from a tip of the micro tube to a target site by first spraying the finely powdered drug and second spraying the fine particles of the biopolymer to coat the drug component layer on the target site, thereby preventing diffusion and leakage of the drug to a location other than the target site.

Specifically, according to the present invention, the drug fine powder is sprayed and applied onto the target site by utilizing the fluid dynamics of the gas, and the drug adhesion surface is then further coated with the fine particle of the biopolymer, thereby ensuring leakage and diffusion of the drug fine powder to a portion other than the target site is prevented.

Further, yet other aspect of the present invention according to claim 11 is a method for administering a drug comprising connecting containers containing two types of respectively different components in series with a micro tube and spraying a drug from a tip of the micro tube to a target site, wherein a larger quantity of the component contained in the vessel that is connected nearer to the tip of the micro tube is sprayed than that contained in the other vessel in the first half of the spraying, and wherein a larger quantity of the component contained in the vessel that is connected at the gas input portion side is sprayed than that contained in another vessel in the second half of the spraying, thereby gradually varying the concentrations of the respectively sprayed components.

Specifically, according to the method of the present invention, the coating layer covering the administered site by the spraying can be formed to have a concentration distribution of the components that has an automatically-formed gradient from the interior side of the administered site to the exterior side thereof. For example, an inner layer in vicinity of an injured surface can be coated with a composition containing a component promoting the healing of the injury at a higher concentration, and the outer layer can be coated with a biopolymer having better sealing properties. Such spray coatings, for example, can be achieved by a method in which two vessels containing fine powder gases or two vessels containing aqueous solutions are coupled in series, and the component from the vessel further from the spray slot is transferred to the nearer vessel, and the two components are gradually mixed to provide a concentration gradient.

Alternatively, in the present invention, a plurality of biopolymer, in particular two types of biopolymers that are water-soluble, exhibiting a viscous nature or be coagulated, can be administered, and in such case, a set of fine particle powder thereof and solution thereof, or a set of solutions thereof can be administered to the target site. Therefore, yet other aspect of the present invention according to claim 12 is a method for administering a biopolymer, wherein two types of biopolymer, which can be dissolved in water to exhibit a viscous nature or be coagulated, are employed, and wherein a set of fine particle powder thereof and solution thereof, or a set of solutions thereof are individually transferred through respective micro tubes by flows of gases, and the set are mixed at a tip of the micro tube, thereby spraying thereof to a target site.

In this case, if the two types of the biopolymer is a set of an anionic biopolymer and a cationic biopolymer, both in a solution state can be combined to exhibit physical properties and bio-combinability that are totally different from those of the single component thereof, and in particular, the increase of viscosity is remarkable. Although the combined compound of the both biopolymers is difficult to be transported through the micro tube due to its high viscosity, the highly viscous gel compound having greater adhesiveness can be sprayed to the target site by transporting one of the biopolymers as a form of fine particle powder with a gas flow or transporting both biopolymers as a form of solution with a gas flow, and mixing thereof when spraying.

Therefore, yet other aspect of the present invention according to claim 13 is the method for administrating a biopolymer according to claim 12, wherein the set of the two types of biopolymers is a combination of an anionic biopolymer and a cationic biopolymer, and yet other aspect of the present invention according to claim 14 is the method for administering a biopolymer according to claims 12 or 13, wherein the biopolymers are selected from a group consisting of synthetic polymers, polysaccharides, peptides and proteins.

More specific aspect of the present invention according to claim 15 is a method for administering a drug for providing a hemostasis of a wounded face or providing a seal, characterized in that two capillary tubes are coaxially provided within a micro tube, and fibrinogen alone or a combined liquid thereof with other coagulation factor and thrombin alone or a combined solution thereof with calcium chloride are injected from one capillary tube and another capillary tube, respectively, into a gas flow in the micro tube, thereby spraying the mixture from a tip of the micro tube to a target site while mixing both solutions.

In such case, further specific aspect of the present invention according to claim 16 is a method for administering a drug for providing a hemostasis of a wounded face or providing a seal, characterized in that a powder containing fibrinogen as a chief constituent alone or a mixed fine powder thereof with a biopolymer and an aqueous solution containing thrombin as a chief constituent are employed, and a mixture thereof are sprayed to a target site.

The powder containing fibrinogen as a main constituent can be a powder containing, for example, fibrin, coagulation factor XIII, fibronectin, aprotinin or the like, and a powder containing thrombin as a chief constituent can be a combined powder of thrombin and calcium chloride.

Further, yet other aspect of the present invention according to claim 17 is a fluidized matrix fine particle powder for use as a drug having sustained releaseability in the methods for administering the drug according to any one of claims 1 to 16, wherein the drug is bound to a biopolymer within a solution via an intermolecular interaction consisting of a coulomb force, a hydrogen bonding and a hydrophobic bonding and pulverized at a lower temperature after drying. In this case, properties of the matrix can be utilized to ensure the sustained release of the drug.

Here, when the biopolymers having different ion charges are mixed, the mixture acquires new physical properties due to containing ionic bonds therein, and the increase of viscosity or the reduction of solubility is remarkable. Therefore, a powder prepared by mixing, formulation-processing or chemically combining one electric charged polymer with a drug having an opposite electric charge is fluidized with gas and is mixed and injected with a biopolymer solution having an opposite electric charge to form a sparingly soluble and sparingly degradable gel or semisolid material, thereby enabling to provide a sustained release to the drug administration target site and coating thereof. Further, the physical properties thereof comprise functional characteristics as a drug for hemostasis, prevention of adhesion wound healing and tissue sealing.

Therefore, yet other aspect of the present invention according to claim 18 is a method for administering a drug for providing a hemostasis of a wounded face or providing a seal, wherein the drug according to claim 17 and a biopolymer having an ionic charge opposite to that of the matrix fine particle powder of the biopolymer according to claim 17 are sprayed to a target site from a tip of a micro tube in a fine particle powder state or a solution state.

In addition, the administration method according to the present invention enables spray-administering of an adhesive and filler employed for treatments of bone in orthopedic surgery. Since the adhesive and the filler employed for treatments of bone in orthopedic surgery are generally administered by mixing the ceramics powder and the liquid binder with a spatula and rubbing the mixture on target site, the internal load is generated therein and uniform surface is seldom formed. However, since the ceramics powder is administered via fluidization and spray-administration according to the administration method of the present invention, the ceramics powder can be precisely administered to a larger defective part of a skull and a defective part of the bone that is caused in a surgical removal operation of cancer, which requires a delicate handling, and thus, forming of the bone substitute can easily be conducted, even if the operation field is narrow.

Therefore, yet other aspect of the present invention according to claim 19 is the method according to any one of claims 2 to 7, wherein the biopolymer is a calcium phosphate-type powder, a hydroxyapatite-type powder or a powder of a glass-type material, which is a bone cement or an artificial bone filler, and wherein a mixed solution of a calcium phosphate-type powder or a hydroxyapatite-type powder and a liquid binder agent, or a mixed solution of glass-type material and an aqueous acids is sprayed from a tip of a micro tube to form a bone substitute at a target site.

BEST MODE FOR IMPLEMENTING THE INVENTION

The following describes the present invention in further detail.

The biopolymer used in the present invention is, in one sense, a polymer having so-called biocompatibility, and as a typical biopolymer is not particularly limited as long as the polymer has functions for hemostasis, prevention of adhesion, prevention of keloid, healing of wounds, closing of wounds, sealing and the like. More specifically, carboxymethyl celluloses, carboxyethyl celluloses, oxycelluloses, agaroses, chitins, chitosans, hyaluronic acids, starches, glycogens, alginates, pectins, dextrans, chondroitin sulfates, gelatins, collagens or the like can be employed, or one or more types of these biopolymers can be employed.

Figure 1:
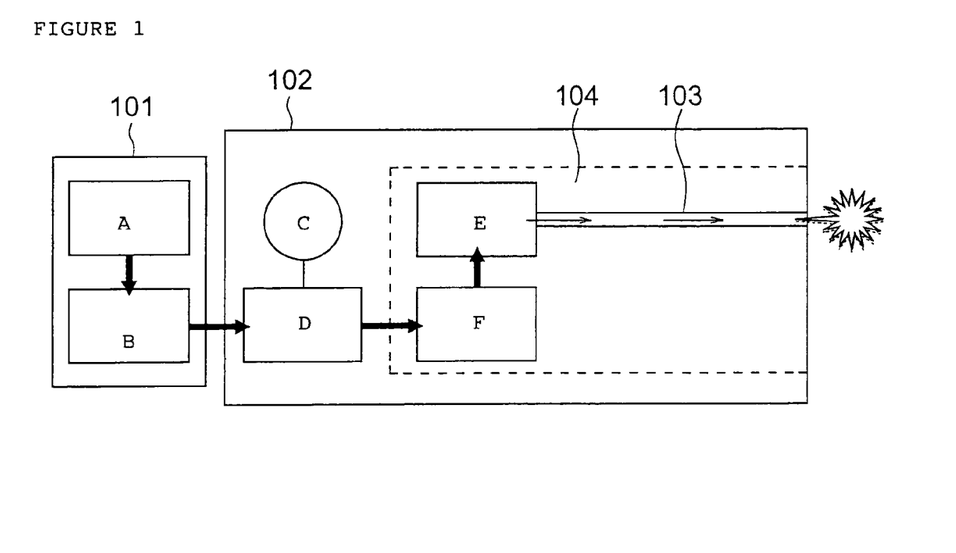
FIG. 1 is a schematic diagram of a fundamental constitution showing the administration method of the present invention.
Figure 2:
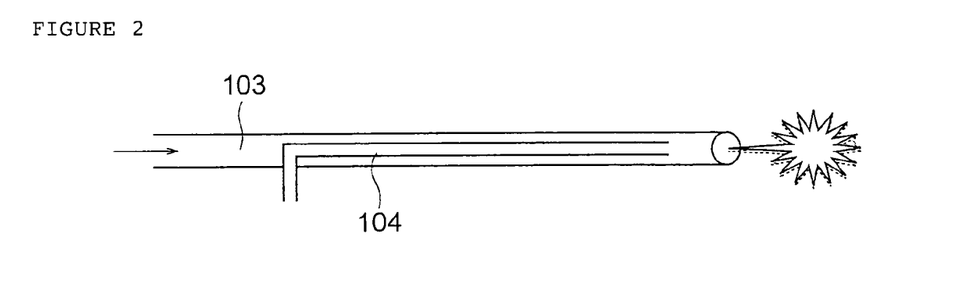
FIG. 2 is a schematic diagram showing the structure of a micro tube, which is provided with a capillary tube disposed coaxially within the micro tube.
Figure 3:
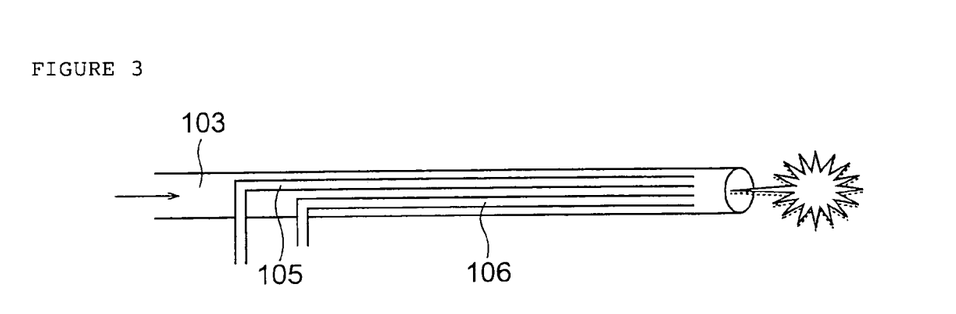
FIG. 3 is a schematic diagram showing the structure of a micro tube, which is provided with two capillary tubes both disposed coaxially within the micro tube.
Figure 4:
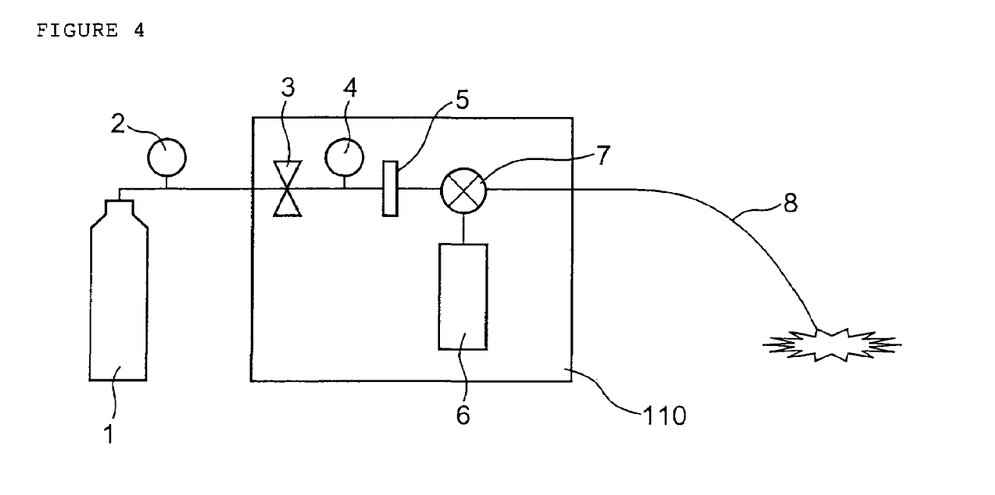
FIG. 4 is a schematic diagram showing the powder gas jet sprayer employed in example 1.
Figure 5:
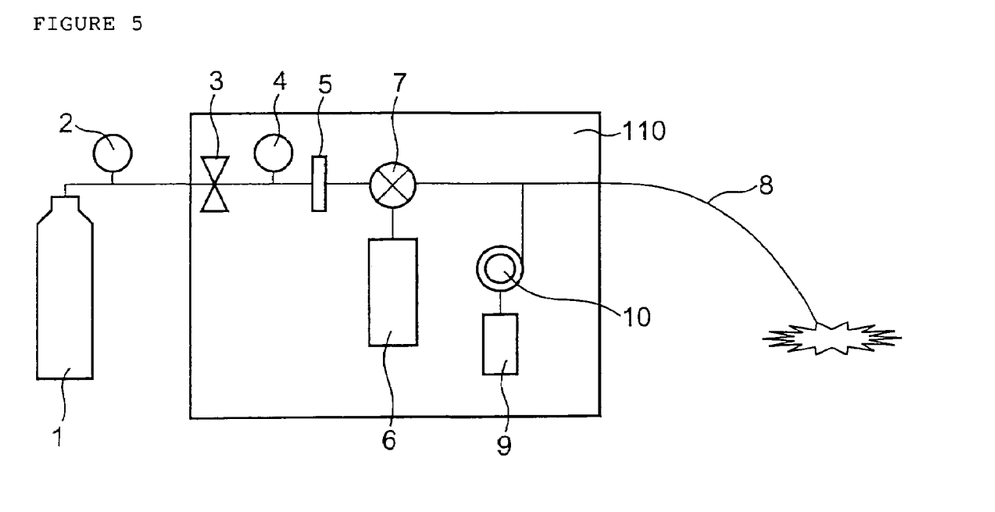
FIG. 5 is a schematic diagram showing the powder gas jet sprayer employed in example 2.
Figure 6:
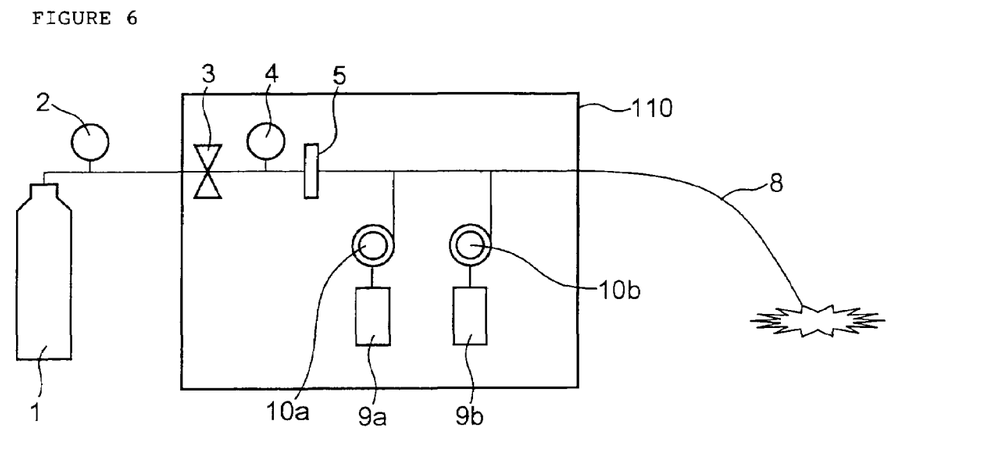
FIG. 6 is a schematic diagram showing the powder gas jet sprayer employed in example 3.

Further, the compound having bioabsorbability can be employed as the biopolymer, and such bioabsorbable materials can be polylactic acids, lactic acid-ethylene glycol copolymers, collagens, agaroses, polyvinyl alcohols, fibrin gels, gelatins, chitins, chitosans, oxycelluloses, carboxymethyl celluloses, pectins, starches, dextrans, agaroses, alginic acids, chondroitins, chondroitin sulfates, fucoses, carrageenans, ethylene-vinyl acetate copolymers, polyglycolic acids, lactic acid-caprolactone copolymers, calcium phosphates, calcium carbonates, hydroxyapatites or the like.

Further, the drugs capable of being administered with the present invention can include various types of drugs, and among these, typical drugs can be drug medicines possessing lower molecular weights, such as bactericides, antibiotic agents, hemostats, anti-tumor drugs and antiphlogistics, peptides such as cell growth factors, cytostatic factors, neurotrophic factors or the like, protein medicines or various types of antibody medicines, vectors containing genes utilized for gene therapy (adenovirus, retrovirus, liposome, hydrogel or the like) or naked DNA or the like.

These drugs can be administered as fine powders or aqueous solutions by the administration method according to the present invention. Among these, in the case that the drug is administered as fine powder with the biopolymer, when the isoelectric point with the biopolymer is dissociated, the adhesion of the drug can be improved and the release ability of the drug from the biopolymer can be decreased by containing ion-bonds or the like therein, thereby providing better sustained release. Therefore, the method also has the advantages of being capable of appropriately selecting the type of biopolymer depending on the type of the drug for administration.

In order to ensure the sustained release of the drug for usage, the powder prepared by the method, in which the drug having an electric charge is previously ion-bonded to a biopolymer having different electric charge in an aqueous solution, then freeze-dried and thereafter pulverized to be unified, can be administered by the administration method of the present invention.

As an alternative approach for providing sustained release, the drug for administration is microencapsulated to form fine particles, and these fine particles, either alone or with a biopolymer, can be administered by the administration method of the present invention.

In the administration method of the present invention, the drug and/or the biopolymer is precisely administered to the target site basically by fluidizing the drug and/or the biopolymer in the carrier gas flow, transferring thereof through the micro tube, and injecting the fine particles of the drug and/or the biopolymer from the tip of the micro tube. Therefore, it is preferable to employ fine particles, which are capable of being fluidized by the drug and/or the carrier gas. Such fine particles can preferably have a particle size distribution, in which roughly 80% particles have particle diameters under 100 μm, and the mean particle diameter is equal to or less than 50 μm.

Here, in the administration method of the present invention, the administered drug and/or biopolymer are not particularly limited to the form of the fine particles, and it is needless to say that even a solution-type thereof can be administered according to the administration method of the present invention.

Although various types of gases are included in the carrier gases available for the present invention, it is preferable to employ carbon dioxide gas or nitrogen gas in view of safety and convenience. It is preferable to use gas-piping facilities in a hospital for the injection gas.

A fluidization of the drug and/or the biopolymer in the administration method of the present invention can preferably be conducted within a blending cell for the gas and the pulverized powder. Further, in order to mix a liquid and the fine powder, which is fluidized with gas, the liquid can be injected into a micro tube via a capillary tube, where the liquid and the powder come into contact and can be mixed. The flow rate of the gas flowing through the micro tube can be at a level that promotes fluidizing a sufficient amount of the gas for spraying the mixture of the drug from the tip of the micro tube, and after setting such a flow rate for the gas, for example, bacteria or the like are removed via passage through a bacteria filter, the powder is fluidized within a powder blending cell, further the fine particles of the drug and/or the biopolymer are transferred through the micro tube, the drug and the like is sprayed from the tip of the micro tube, thereby being sprayed to the targeted administering site, in particular the administration site in a living body.

The administration method of the present invention will be described in detail as follows, with reference to FIG. 1 that shows a schematic diagram thereof.

The FIG. 1 schematically shows a fundamental configuration for the administration method of the present invention. Specifically, a fluidizing gas such as carbon dioxide gas or nitrogen gas flows from a gas supply source (A) of an outside facility (101), and after the pressure thereof is adjusted via a pressure regulating valve (B), the flow is modulated by a gas flow rate control valve (D) and a flow meter (C) on the apparatus portion (102), and then, the bacteria included in the gas are removed by a bacteria filter (F), and thereafter, the flow is eventually supplied to a powder-gas mixing cell (E), where the drug and/or the biopolymer are fluidized.

The fluidization of the drug and/or the biopolymer in the blending cell can preferably be conducted within the blending cell that is a quantification mixer comprising a rolling shaker, a rotary shaker or a supersonic wave shaker, and the powder of the drug and/or the biopolymer is uniformly mixed and fluidized by the gas in the interior of the quantification mixer (blending cell). The mixed powder fluidized by the gas is then transferred through the micro tube (103) by the gas to be sprayed from the tip of the micro tube (103). In this case, the bacteria filter-blending cell-micro tube portion of the apparatus portion (102) can be a disposable portion (104), which is easily replaced depending upon the type of the drug and/or the biopolymer suitable for the administration target.

When the drug and/or biopolymer to be administered by the administration method described above is in a solution form, a capillary tube (104) is provided coaxially within the micro tube (103), and when the liquid-type drug and/or biopolymer is injected from the tip of the capillary tube toward the gas flow in the micro tube (shown by an arrow in the figure), the liquid is dispersed by the gas flow to form a mist, and then the mist is sprayed from the tip of the micro tube, thereby enabling the spraying thereof onto the target site. A schematic structure of the micro tube, which can be used for in this case, is shown in FIG. 2.

Alternatively, two or more types of the liquids of the drug and/or the biopolymer can be mixed for administering via the administration method of the present invention. In such case, two or more of the capillary tubes (105,106) are installed coaxially within the micro tube (103) as required, and the individual solutions of the drug and/or the biopolymer are injected into the gas flow in the micro tube (shown by an arrow in the figure) from the tip of the capillary tube to form a mist, and the mist can be sprayed from the tip of the micro tube. The schematic structure of the micro tube is shown in FIG. 3.

Alternatively, a modification of the administration method of the present invention can employ a small cylinder as the supply source of the fluid gas. Further, if a micro tube is coupled to an aerosol, and a capillary tube is combined with the micro tube, achieving a miniaturization thereof or providing a disposable application is possible. In this case, two types of aerosols are combined and coupled via a nozzle, and two types of drug and/or biopolymer are simultaneously injected from the respective aerosols and mixed in the coupled portion, and then the drug and/or the biopolymer can be sprayed from a tip of an integrated micro tube.

EXAMPLES

The present invention is further described in detail by the following illustrating examples.

Example 1

A schematic diagram of the powder gas jet sprayer employed in Example 1 is shown in FIG. 4.

This apparatus, for example, adjusts pressure of carbon dioxide gas from a gas supply source (1) such as carbon dioxide gas cylinders or the carbon dioxide gas pipe supply network within hospitals or the like using a pressure regulation valve (2), and thereafter the flow of gas is modulated in the apparatus (110) by a gas flow valve (3) and a flow meter (4), then bacteria contained in the gas are removed by the bacteria filter (5). The gas and the powdered drug and/or the biopolymer are fluidized within a quantification mixer (7) containing a shaking device (6), and then transferred through the micro tube (8) with the gas, and eventually sprayed from the tip of the micro tube.

Fine powder of a lysozyme chloride, which is an anti-inflammatory enzyme preparation as a drug, is mixed with a biopolymer of carboxymethyl cellulose that has an advantageous effect of providing hemostasis and preventing adhesion at a mixing weight ratio of 1:20, and thereafter a fluidization thereof is conducted, and then the spraying and the application thereof to an organization isolation face after surgical operation is conducted from the tip of the micro tube. As such, hemostasis, anti-inflammatory effect and adhesion prevention can be provided.

Example 2

A schematic diagram of the powder gas jet sprayer employed in the Example 2 is shown FIG. 5. Here, the signs appearing within the diagram have the same meaning as those appearing in FIG. 4.

This apparatus functions in a similar manner to Example 1, in that it adjusts pressure of carbon dioxide gas from a gas supply source (1) such as carbon dioxide gas cylinders or the carbon dioxide gas pipe supply network within hospitals or the like using a pressure regulation valve (2), and thereafter the flow of gas is modulated in the apparatus by a gas flow valve (3) and a flow meter (4), then bacteria contained in the gas are removed by the bacteria filter (5). The gas and the powdered drug and/or the biopolymer are fluidized within a quantification mixer (7) containing a shaking device (6), and then transferred through the micro tube (8) with the gas, and eventually sprayed from the tip of the micro tube, and additionally, a capillary tube (not shown) is installed within the micro tube (8), for example as shown in FIG. 2, and a solution of the drug and/or the biopolymer is injected via a pump (10) from a fluid container (9).

10 g of carboxymethyl cellulose is added as a biopolymer into a powder-gas mixing cell. 7 ml of 10% cationic cellulose aqueous solution is added into a liquid vessel (9) that is connected to a pump (10), and the powder is fluidized at another place, and then the cationic cellulose solution is injected from the capillary tube into the micro tube (8) and is mixed, and eventually the mixture is sprayed and applied to an organization isolation face after surgery from the tip of the micro tube. These two components start mutually coupling simultaneously when they are mixed, and they exhibit a viscosity, and then the mixture is firmly adhered to the organization isolation surface, where the adhered mixture is not melted, thereby exhibiting better sealing effect without dispersal thereof by body fluids to promote a hemostasis, prevention of adhesion and wound healing.

Example 3

A schematic diagram of the powder gas jet sprayer employed in Example 3 is shown in FIG. 6. Here, the signs appearing within the diagram have the same meaning as those appearing in FIG. 4 and FIG. 5.

This apparatus functions in a similar manner to Example 1 and Example 2, in that it adjusts pressure of carbon dioxide gas from a gas supply source (1) such as carbon dioxide gas cylinders or the carbon dioxide gas pipe supply network within hospitals or the like using a pressure regulation valve (2), and thereafter the flow of gas is modulated in the apparatus by a gas flow valve (3) and a flow meter (4), then bacteria contained in the gas are removed by the bacteria filter (5). Then, the apparatus is designed so that it can transfer fluids through the micro tube (8), and spray such fluids from the tip of the micro tube, and further, two capillary tubes (not shown) are installed within the micro tube, as shown in FIG. 3, for example, and solutions of the drug and/or the biopolymer are injected via the pumps (10a, 10b) from the liquid vessels (9a, 9b), respectively.

As sealing agents for surgery usage, 5 ml of 10% fibrinogen aqueous solution and 5 ml of thrombin 2500 unit aqueous solution are contained in different vessels (9a, 9b), respectively, and the injections are conducted into the micro tube via pumps (10a, 10b) through capillary tubes from these vessels, and they are mixed with the gas to form a mist, and then the mixture of fibrinogen and thrombin is sprayed from the tip of the micro tube to a target site. This provides that fibrin created on the injured surface can be utilized as a hemostasis and sealing agent.

Example 4

Figure 7:
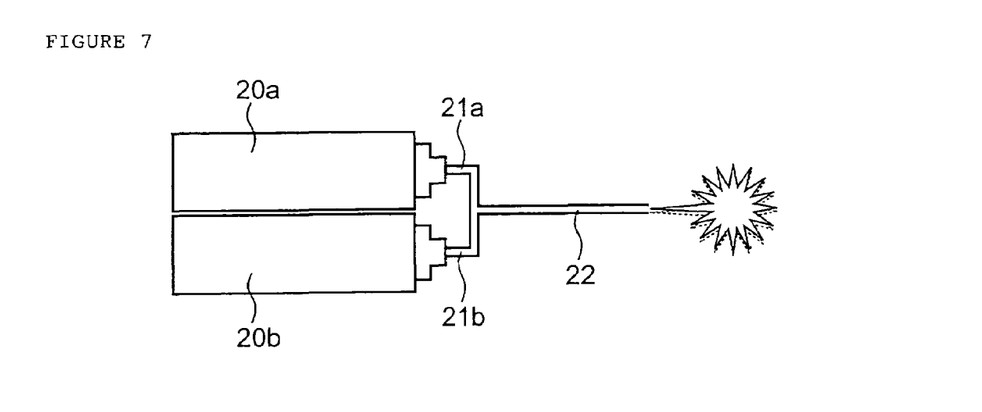
FIG. 7 is a schematic perspective view of a gas jet sprayer that utilizes two aerosols employed in example 4.

A schematic front elevation view of the gas jet sprayer employing two aerosols used in this example is shown in FIG. 7. In this example, a plurality of (two, in this example) aerosols, which are small cylinders (20a, 20b), are used as sources of fluidizing gas supply, and two aerosol vessels are connected to micro tubes (21a, 21b), and the drug and/or the biopolymer is sprayed from a tip of a micro tube (22), which is formed by convergingly integrating the two micro tubes. Preferably, coupling of the micro tubes to the aerosols can be conducted by installing the double-coupled actuators, which are formed by integrating two aerosol vessels having push-down valves with a thermal shrinkage tube.

10 ml of 10% aqueous solution of fibrinogen and 5 ml of 2500 unit aqueous solution of thrombin were respectively filled in the 10 ml aerosol vessels as stock solutions, and further nitrogen gas was filled therein at a pressure of 4 kg/cm$^2$ as injection agents. Aqueous solution containing fibrinogen and aqueous solution containing thrombin were injected from respective aerosol vessels by depressing push-down buttons of the aerosol vessels, and mixed by an actuator, transferred in a form of mist through the micro tube, and eventually sprayed from the tip of the micro tube to a target site to be provided with a hemostasis.

INDUSTRIAL APPLICABILITY

As described above, the present invention provides a method for precisely administering a finely powdered drug to a target site, in particular to a target site in a body cavity, by utilizing fluidization and injection with a gas and injection with a fine tube (a micro tube) and also to provide a method for administering a biopolymer itself as the drug or administering a drug with a biopolymer as a carrier. Specifically, the administration method of the present invention provides an advantageous effect of applying a drug or a biopolymer regardless of the size, the shape and the position of the application site and that is capable of providing the target results thereof such as providing a hemostasis, preventing adhesion, preventing a keloid, healing a wound, closing a wound, providing a seal or the like in a easier way.

Specifically, the administration method according to the present invention has a configuration that includes pulverizing the drug and the biopolymer to reduce the unit weight of the pulverized powder, fluidizing thereof with the carrier gas, transferring thereof through the micro tube, and injecting the finely powdered drug and the biopolymer from the tip of the micro tube, and, being so configured, the drug and the biopolymer can be precisely administered through a narrow space from the surface of the body to the target site positioned in a deeper part of the body to which the administration thereof has been conventionally impossible.

Further, the present invention is the administration method, characterized in that the method comprises: mixing fine particles of the biopolymer as carrier with the finely powdered drug and fluidizing the mixture; transferring thereof through the micro tube using a gas; and spraying the mixed finely powdered biopolymer and the drug to the target site from the tip of the micro tube so as to improve the adhesiveness than using the drug alone, and thus, this configuration provides advantageous effects, in which the finely powdered drug, with the fine particles of the biopolymer as a drug carrier, can be mixed and administered to the target site by fluid force and spray force of the gas.

Further, the method for administering a drug according to the present invention comprises: conducting a fluidization of biopolymer fine powder and a fluidization of a drug fine powder in different vessels; transferring the respective fine powders with a gas flow through a micro tube; spraying the fine drug powders from a tip of the micro tube to a target site; and thereafter spraying the fine particles of the biopolymer to coat the drug component layer on the target site, and therefore the advantageous effects of preventing a diffusion of the drug to a portion other than the target site can be obtained.

Alternatively, in the present invention, a plurality of biopolymer, in particular two types of biopolymer that can be dissolved in water to exhibit a viscous nature or be coagulated can be administered, and in such case, the advantageous effects can be obtained, in which a set of fine particle powder thereof and solution thereof, or a set of solutions thereof can be administered to the target site.

What is claimed is:

1. A method for administering a biopolymer having hemostatic or adhesion preventing functions, comprising the steps of:
   fluidizing fine particles of the biopolymer having hemostatic or adhesion preventing functions with a gas to prepare a homogenous mixed-phase fluid;
   transferring the mixed-phase fluid through at least one micro-tube by flowing the gas;
   mixing a liquid with the mixed-phase fluid, the liquid being selected from the group consisting of a saline solution, an infusion solution, an aqueous solution of a drug and an aqueous solution of a biopolymer; the liquid being injected into the micro-tube thorough at least one inner tube so that the liquid is mixed with the mixed-phase fluid, wherein the inner tube is configured to be within the micro-tube;
   spraying the mixed liquid and the mixed-phase fluid toward a target site from an open tip of the micro-tube; wherein the mixed liquid and the mixed-phase fluid become a gel compound after the liquid and the mixed-phase fluid are mixed;
   whereby the fine particles of the biopolymer are capable of being sprayed as a gel compound toward the target site to provide a seal upon the target site.

2. The method in accordance with claim 1, wherein the biopolymer is carboxymethyl cellulose.

3. The method in accordance with claim 1, wherein the biopolymer is carboxymethyl cellulose and the liquid is cationic cellulose aqueous solution.

4. The method in accordance with claim 1, wherein the step of fluidizing fine particles of a biopolymer with a gas is
a step of fluidizing a finely powdered drug and fine particles of a biopolymer with a gas to prepare a homogenous mixed-phase fluid.

5. The method in accordance with claim 1, wherein the liquid comprises an aqueous solution of drug.

6. The method in accordance with claim 1, wherein the biopolymer comprises at least two types of biopolymers, the two types of biopolymers being a combination of an anionic biopolymer and a cationic biopolymer.

7. The method in accordance with claim 1, wherein the gas is carbon dioxide gas or nitrogen gas.

8. The method in accordance with claim 1, wherein the liquid comprises fibrinogen aqueous solution and thrombin aqueous solution.

9. A method for administering a biopolymer having hemostatic or adhesion preventing functions, comprising the steps of:
fluidizing fine particles of the biopolymer having hemostatic or adhesive preventing functions with a gas to prepare a homogenous mixed-phase fluid, wherein the biopolymer comprises at least two types of biopolymers, the two types of biopolymers being a combination of an anionic biopolymer and a cationic biopolymer;
transferring the mixed-phase fluid through at least one micro-tube by flowing the gas;
mixing a liquid with the mixed-phase fluid, the liquid being selected from the group consisting of a saline solution, an infusion solution, an aqueous solution of a drug and an aqueous solution of a biopolymer; the liquid being injected into the micro-tube thorough at least one inner tube so that the liquid is mixed with the mixed-phase fluid, wherein the inner tube is contained within the micro-tube;
spraying the mixed liquid and the mixed-phase fluid toward a target site from an open tip of the micro-tube; wherein the mixed liquid and the mixed-phase fluid become a gel compound after the liquid and the mixed-phase fluid are mixed;
whereby the fine particles of the biopolymer are capable of being sprayed as a gel compound toward the target site.

10. A method for administering a biopolymer having hemostatic or adhesion preventing functions, comprising the steps of:
fluidizing fine particles of the biopolymer selected from the group consisting carboxymethyl celluloses, carboxyethyl celluloses, oxycelluloses, agaroses, chitins, chitosans, hyluronic acids, starches, glycogens, alginates, pectins, dextrans, chondroitin sulfates, gelatins and collagens with a gas to prepare a homogenous mixed-phase fluid;
transferring the mixed-phase fluid through at least one micro-tube by flowing the gas;
mixing a liquid with the mixed-phase fluid, the liquid being selected from the group consisting of a saline solution, an infusion solution, an aqueous solution of a drug and an aqueous solution of a biopolymer; the liquid being injected into the micro-tube thorough at least one inner tube so that the liquid is mixed with the mixed-phase fluid, wherein the inner tube is configured to be within the micro-tube;
spraying the mixed liquid and the mixed-phase fluid toward a target site from an open tip of the micro-tube; wherein the mixed liquid and the mixed-phase fluid become a gel compound after the liquid and the mixed-phase fluid are mixed;
whereby the fine particles of the biopolymer are capable of being sprayed as a gel compound toward the target site to provide a seal upon the target site.

* * * * *